United States Patent [19]

King

[11] 4,036,589
[45] July 19, 1977

[54] DETERMINING THE CONCENTRATION OF A BIOCIDE ADDITIVE IN A LIQUID

[75] Inventor: Robert Daniel King, Mill Valley, Calif.

[73] Assignee: J. R. Schneider Co., Inc., Tiburon, Calif.

[21] Appl. No.: 668,868

[22] Filed: Mar. 22, 1976

Related U.S. Application Data

[63] Continuation-in-part of Ser. No. 588,517, June 19, 1975, abandoned.

[51] Int. Cl.² ............... B01D 17/04; G01N 33/16
[52] U.S. Cl. .................. 23/230 B; 252/327; 252/329
[58] Field of Search ............. 23/230 B, 253 TP; 252/327, 329, 358

[56] References Cited

U.S. PATENT DOCUMENTS

| 1,771,096 | 7/1930 | Penn | 252/329 |
| 2,504,019 | 4/1950 | Hall | 252/329 |
| 3,673,183 | 6/1972 | Erickson | 23/253 TP X |

OTHER PUBLICATIONS

Hoffpavir et al. Anal. Chem. 15,605(1943).
M. Beroza, Anal. Chem. 26, 1970(1954).
Sawicki et al. Anal. Chem. 34,1460(1962).
Skelley et al., Clin. Chem. 19,146,156(1973).
Aloe Chemical Catalog 103,1952, pp. 127, 129, 1010.

*Primary Examiner*—Robert M. Reese
*Attorney, Agent, or Firm*—Owen, Wickersham & Erickson

[57] ABSTRACT

A method and a kit for testing the biocide concentration of a liquid containing a biocide of the type which breaks down in acidic aqueous solution to liberate formaldehyde. A strong aqueous acid is added to the liquid, and a modified Schiff's reagent is also added. Time is given for color to develop, and then the color intensity of the solution is read. In instances where oil-water emulsions or latices are involved, the emulsion is broken before adding the Schiff's reagent.

14 Claims, 5 Drawing Figures

DETERMINING THE CONCENTRATION OF A BIOCIDE ADDITIVE IN A LIQUID

CROSS-REFERENCE TO RELATED APPLICATION

This application is a continuation-in-part of application Ser. No. 588,517, filed June 19, 1975, now abandoned.

BACKGROUND OF THE INVENTION

This invention relates to a method and a kit for determining the biocide concentration in a liquid containing a biocide of the type which liberates formaldehyde in water, especially under acid conditions.

A good example of one field where the invention is particularly useful is that of detecting the biocide concentration in a liquid coolant-lubricant of the type used for rolling sheet metal or forming cylinders from sheet metal, to which certain biocides have been added. Microorganisms, including both bacteria and fungi, are generally present in all such coolants involving water solutions or water emulsions of mineral-oil based compositions or synthetic lubricants. Unless the growth rate of these microorganisms is carefully controlled, the productive coolant life can be shortened considerably; replacing the coolants usually results in excessively high maintenance costs. Therefore, it is good practice to add a suitable biocide to the coolant. As long as the biocide is active, the coolant is preserved from attack by microorganisms.

The problems have been to determine whether the biocide is within the right concentration range after the biocide-containing coolant has been in use for some time. To do this it is necessary to determine the concentration of the biocide. The biocidal ability of the fluid may be exhausted or it may still be present. If present, it is not only wasteful to add more of the biocide, but it also may lead to poisoning the environment. Overuse of the biocide is quite undesirable, but underuse also has serious consequences.

It has been found that some of the most useful biocides break down in water, and especially in acid solutions, to liberate formaldehyde, which appears to be in proportion to the biocidal potentiality of the biocide. In fact, it may well be that liberation of formaldehyde is the biocidal activity of some or all of these biocides.

For example, one biocide is 1-(3-chloroallyl)-3,5,7-triaza-1-azoniaadamantane chloride. This material, and some others like it (such as hexahydro 1,3,5-triethyl-S-triazine and hexahydro 1,3,5-tris-(2-hydroxyethyl)-S-triazine), break down to yield a number of compounds including, ultimately, water, ammonia, carbon dioxide, and chlorine. However, the intermediate degradation yields formaldehyde in a mole-to-mole ratio, as well as some amines, amine formates, hexamethylenetetramine methyl chloride and hexamethylenetetramine hydrochloride. Of these compositions, formaldehyde is easily detected by a procedure which I have developed.

Coolants and cutting oils with such biocides can be tested for formaldehyde liberation, but when the coolant or cutting oil is an oil-in-water emulsion it is too opaque for testing color intensity in a simple colorimeter. The same is true for testing latex paints containing biocides. Moreover, even though the test (without a colorimeter) can be rather straightforward when such coolants are fresh, problems arise when they have been in use for a while. The reading of color intensity by any method is then made inaccurate by the presence of a grayish cast in the coolant, which is apparently due to non-filterable metallic fins that become associated with oil droplets, or perhaps are in a free state within the coolant. The amount of grayness in even the same coolant varies from customer to customer and from time to time, with the amount and conditions of use of the coolant. I have discovered that this problem can be overcome by the development of a two-phase breaking and clearing solution, which leads to especially good results.

SUMMARY OF THE INVENTION

I have found that the biocide concentration in a liquid containing such biocides can be detected with the aid of a modified Schiff's reagent. This test applies both to water-oil emulsions, latices, and to aqueous solutions. By adding a strong acid and the modified Schiff's reagent to a sample, a reaction is started which develops over a period of some minutes to a maximum blue or violet color. The intensity of this color after a predetermined time interval can be used to indicate the biocide concentration remaining in the substance.

An oil-water emulsion that contains a biocide of the type that liberates formaldehyde in water can be tested for biocide concentration, even when the emulsion also contains unfilterable opaquing matter, by adding a predetermined sample of the emulsion to a test tube which contains a bottom aqueous phase of a solution for breaking the emulsion, such as a water solution of magnesium sulfate and sulfuric acid, and a top phase of a non-water-miscible solvent for the oil. After shaking the test tube vigorously to ensure good particle contact, the modified Schiff's reagent is immediately thereafter added to the test tube and mixed with the liquid.

The modified Schiff's reagent contains rosaniline hydrochloride (basic fuchsin), sodium bisulfite and hydrochloric acid.

After addition of the modified Schiff's reagent, the test tube is put in a rack, and a predetermined amount of time is allowed to elapse; the proper time interval can easily be standardized to develop substantially the maximum color strength. When the reaction extends much beyond this time interval, the color begins to lighten. One can read the intensity of the color, which is blue, violet, or blue-violet, on a suitable colorimeter, or one can compare it with comparison samples or color chips.

Other objects, advantages, and features of the invention will become apparent from a description of a preferred form thereof.

DESCRIPTION OF A PREFERRED EMBODIMENT

Figure 1:
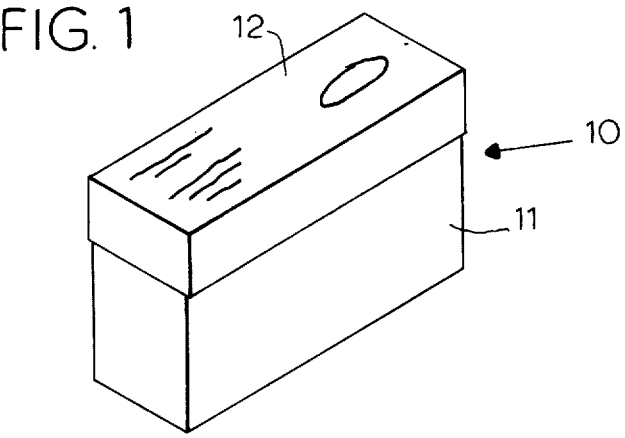
FIG. 1 is a view in perspective of a kit embodying the principles of the invention.

A preferred embodiment of the invention relates to the testing of an oil-water emulsion that contains the biocide 1-(3-chloroallyl)-3,5,7-triaza-1-azoniaadamantane chloride. The test may be done in exactly the same way for such emulsions as contain other biocides, such as hexahydro 1,3,5-triethyl-S-triazine or hexahydro 1,3,5,tris-(2-hydroxyethyl)-S-triazine. The test may be varied slightly when testing other biocides that release formaldehydes in acidic aqueous solution, as well as for testing other biocides giving the general type of reaction. I know of no biocide of the type that releases formaldehyde in acidic aqueous solutions with which the invention will not work.

For this purpose, a standard modified Schiff's reagent is desired. While other concentrations and formulations can be used, good results have been obtained by preparing this reagent as follows:

Dissolve 0.2 g, of pure rosaniline hydrochloride in 120 ml of hot distilled water (e.g., about 95° C.). Cool the solution (e.g., to about 25° C.) and filter (e.g., Whatman No. 5 filter paper), and then dissolve 2 g. of ahydrous sodium bisulfite (or equivalent thereof of sodium bisulfite containing water of crystallization). To this solution add 2 ml of concentrated hydrochloric acid. Dilute the resulting solution to 200 ml with distilled water. The reagent is ready for use after standing at room temperature for about 1 hour. After that it may be stored in well-filled amber bottles, under refrigeration, at temperature no higher than 15° C.

Where there is no problem with suspended colloidal material that affects the degree of transparency of the liquid, then a test may be made, for example, by taking a sample of 5 ml of the solution, adding 1 ml of concentrated sulfuric acid, allowing the mixture to cool to about room temperature, and then adding 5 ml of the modified Schiff's reagent. In about 10 to 15 minutes, a blue-violet color develops, to an intensity which may then be read on a colorimeter or visually compared with standards. If very much formaldehyde is present (i.e., if the concentration of the biocide is high), the color may be too dark for proper recognition, and the test is better made with a dilute sample, diluted to a known degree with water. Quantitative results may be obtained by calibrating the solution in relation to known concentrations of formaldehyde. Sensitivity of this test is better than one part per million, and comparisons may either be made with a set color sample or a test tube sample of a known concentration treated at the same time, or a colorimeter properly calibrated may be used. With paints it may be difficult, impossible, or impractical to use a colorimeter, but comparison with color chips will give satisfactory numerical indication of values.

When emulsions containing non-filterable aluminum fines or similar material that affect the opaqueness of the emulsion, or in any event when a colorimeter is to be used, it is necessary to break the emulsion and clear it. This is true also with latex-base paints. A two-phase system may be prepared by first adding an acid solution of magnesium sulfate and then placing over it a suitable oil solvent which is not miscible with water. The lower phase may be prepared by mixing magnesium sulfate ($MgSO_4 \cdot 7H_2O$) at a rate of 50 grams per 100 ml of distilled water, and then adding to that solution 25 ml of concentrated sulfuric acid. The final concentration of sulfuric acid is, in this instance, 3.6N. The upper phase to be used may comprise 1-butanol, or other suitable alcohol which is not miscible with water or appreciably soluble therein and which is sufficiently liquid to dissolve the oil, or, in other words, a solvent for the oil which is immiscible with water.

In this instance, the test may comprise a sample of three-tenths of a milliliter (0.3 ml) of the coolant or cutting oil or paint which is added to a breaking and clearing solution comprising 2½ ml (2.5 ml) of the magnesium sulfate-sulfuric acid solution described above, over which is 4 ml of 1-butanol. After introduction of the sample, the test tube is capped and shaken vigorously. This procedure breaks the coolant emulsion, and the oil phase of the coolant dissolves in the 1-butanol, which also extracts other opaquing material, while the aqueous phase of the coolant (which contains the biocide) remains in the aqueous or lower phase of the breaking and clearing solution. Preferably, immediately after shaking and before settling, 5 ml of the modified Schiff's reagent, as described, are added, the tube capped and inverted twice. The test tube is then put in a rack to stand, and the two phases separate, the oil and other opaquing matter passing into the upper phase while the biocide is carried in the lower phase. The sulfuric acid in the aqueous phase degrades the biocide to formaldehyde.

Upon standing, not only does the separation of phases occur, but in about 30 minutes a blue or blue-violet or violet color will develop to a suitable intensity. To give reproducible, accurately comparable results, and at room temperature (about 25° C.), some standard time, such as 15, 20, 30, or 45 minutes, may readily be determined as a time interval giving a suitable color intensity. The test tube may be heated if shorter time intervals are desired, but in any event, all tests should be made under the same conditions if quantitative results are desired. I have found that with the solution described, exactly as given, 30 minutes is a good standard time at 25° C. The degree of color is dependent upon the amount of formaldehyde and therefore indicates the concentration of the biocide. A colorimeter reading can be made, and the colorimeter can either be directly calibrated, or a calibration chart, such as a standard graph may be prepared or supplied by the manufacturer. It is preferred, of course, to read the blue color through an orange or a yellow light. With paints, colorimetry is usually impractical, but comparison with standardized color chips gives acccuracies within 0.2%, instead of the 0.1% obtained where colorimetry can be used.

Other strong acids may be substituted for sulfuric acid. For example, nitric, hydrochloric, phosphoric and acetic acid, advantageously at concentrations equivalent to that used for sulfuric acid (3.6N) will work. However, each acid reacts at a different rate, and some result in producing a slightly different color. Sulfuric acid is the preferred acid since it gives the quickest reaction and produces a desirable color which can be read by a relatively unsophisticated colorimeter.

Other alcohols than 1-butanol may be used. For example, aliphatic alcohols having four to 10 carbon atoms are feasible. For example, amyl, pentyl, and 2-octanol give results equivalent to 1-butanol. 1-Butanol is desired since it is the least expensive and gives adequate results.

Figure 2:
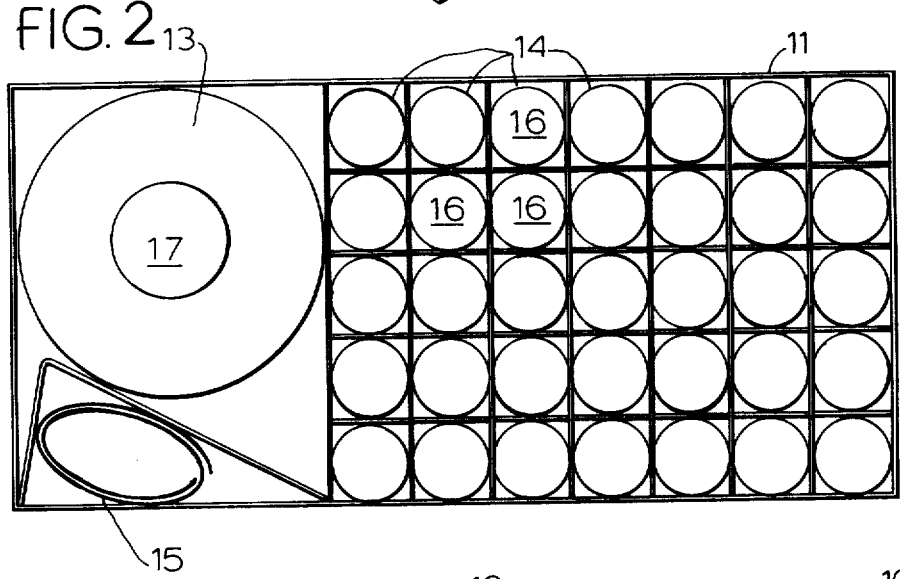
FIG. 2 is an enlarged top plan view of the kit with the cover removed.
Figure 3:
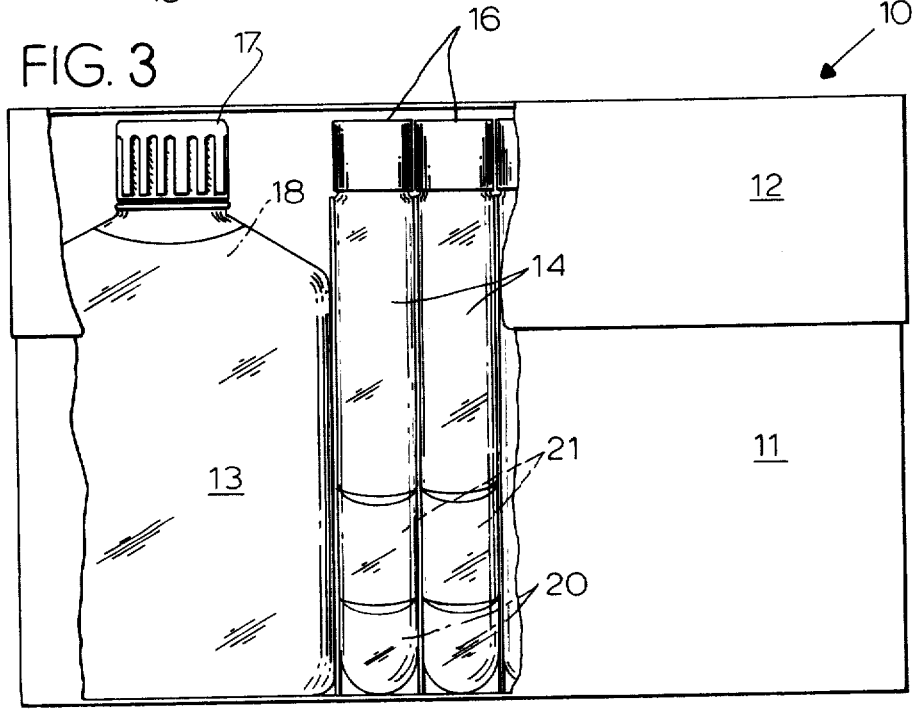
FIG. 3 is a view of the kit in side elevation with a portion of the container wall cut away to show some of the contents.

The drawings show a kit which may be utilized in the invention. Thus, in FIG. 1 a kit 10 is shown embodying a container 11 with a top or lid 12. Inside the container 11, as shown in FIGS. 2 and 3, are a bottle 13, a series of test tubes 14, and a sheet of color chips or a graph 15. Each test tube 14, which may be glass, is provided with a suitable stopper or cover 16. The bottle 13 may be of plastic or glass and should have a good stopper or screw cap cover 17 in order to prevent access by oxygen to the interior. The bottle 13 is filled with modified Schiff's reagent 18, and it should be stored under refrigeration, but brought to room temperature before using it in a test.

It has been found through experimentation that test tubes obtained from commercial sources do not allow for a clean separation of oil emulsion, usually resulting in an oil film coating the tube in the area where it is to be analyzed in the colorimeter. Thus, an accurate reading could not be obtained. This problem is solved by cleaning the test tubes 14 as follows before introducing the liquids and packaging them in the kits 10. Each test tube 14 is immersed in a 3% potassium hydroxide solution and then rinsed thoroughly in de-ionized water. After the tubes 14 are dried, they are immersed for 5 seconds in a 1% silicone solution (e.g., Siliclad by Clay-Adams) and then are rinsed one time in distilled water. Preferably, they are then air dried overnight.

Figure 4:
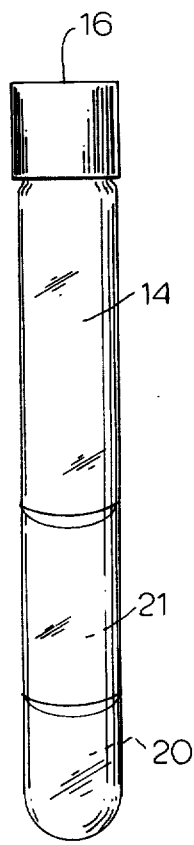
FIG. 4 is a further enlarged view in elevation of one of the test tubes from the kit.
Figure 5:
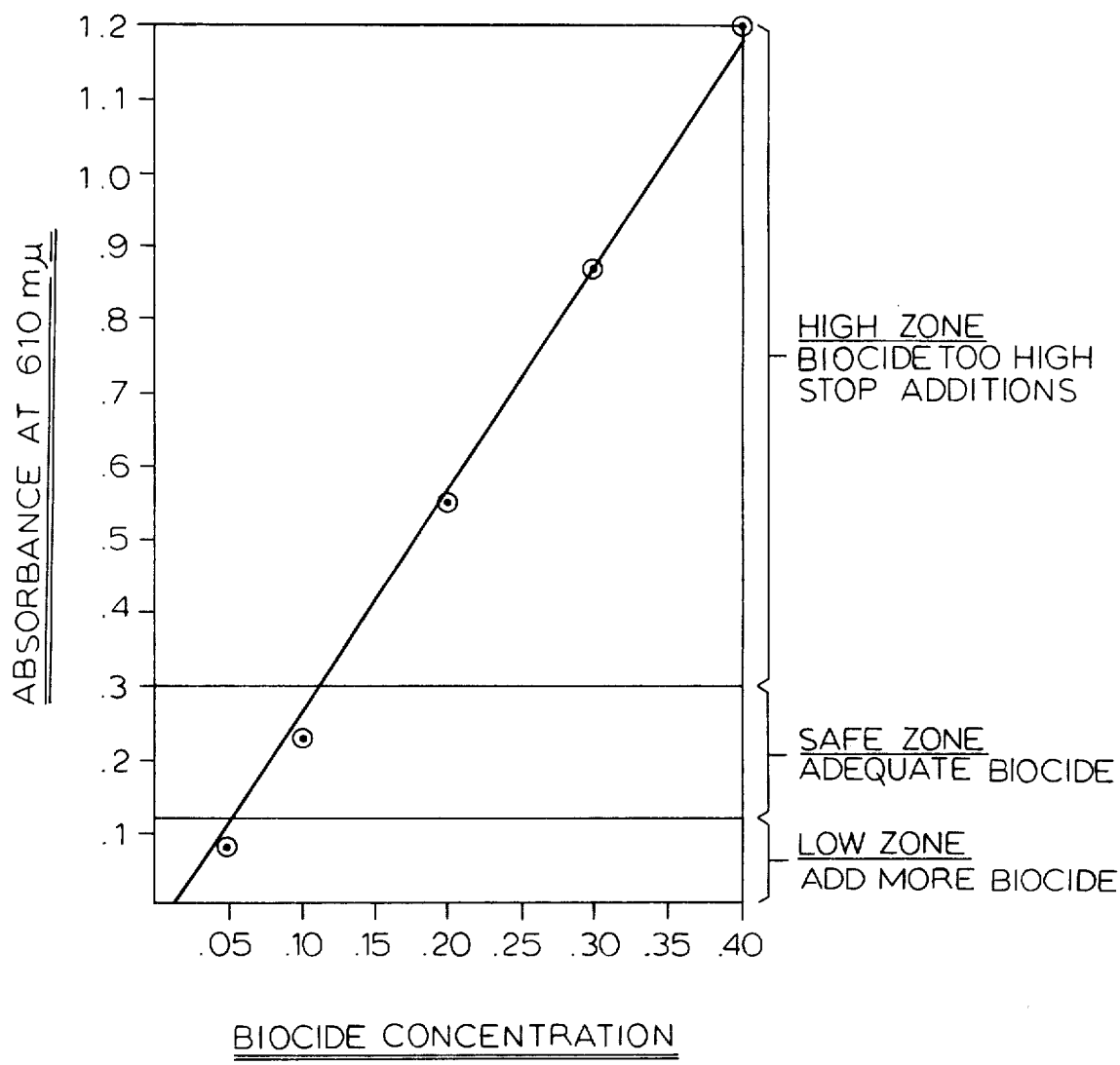
FIG. 5 is a view of a typical graph of the type furnished in each kit.

Each test tube 14 is partially filled with an aqueous phase 20 and an oil phase 21. The aqueous phase 20 includes water and the strong acid, such as sulfuric acid, and magnesium sulfate. The oil phase 21 as packaged includes the non-water-soluble oil solvent, such as 1-butyl alcohol (1-butanol). The liquids will normally be separated into the two phases 20 and 21 as shown in FIGS. 3 and 4.

In use, the investigator removes one test tube 14 from the kit 10, unscrews the cover 16 (or removes the stopper in case that is used as an alternative), and inserts, with the aid of a pipette or other suitable equipment, the sample to be investigated. Directions accompanying the kit 10 are followed exactly as to volumes, so that the operator knows what to do and how to match the volume of the sample to the contents of the test tube 14. After inserting the sample, he then recovers the test tube 14, as by screwing on the cover 16, and then shakes the test tube 14 vigorously to mix the contents well. He next introduces, as with the aid of a pipette or other suitable measuring device, a specified quantity of the modified Schiff's reagent 18, and then lets the test tube 14 stand in a rack for the specified time interval, which may be 30 minutes.

The kit 10 enables the user to perform his own tests rapidly with a minimum of difficulty. Each test tube 14 includes exactly the correct amount of acid, water, magnesium sulfate, and 1-butyl alcohol, and the Schiff's reagent 18 is Properly mixed. All the operator needs to do is to follow the directions accompanying the kit 10, which involve measuring two amounts, shaking, and letting the material stand.

The operator then is able to compare the color developed in the aqueous phase 20 with a standard color on cardboards, i.e., color chips, which may be furnished in the kit 10 in lieu of the graph 15, or uses a colorimeter which will read the density of color developed and then compares that reading with the graph 15 to obtain the quantitative interpretation.

More specifically, a typical use of the kit 10 is as follows: The bottle 13 is stored under refrigeration, and before use the reagent bottle 13 is removed from the refrigerator and allowed to reach room temperature, typically about 2 hours; then the color reagent bottle 13 may be uncapped, and a test tube 14 may be uncapped and placed in a test tube rack. Using a pipetting gun and 1-ml tips, the tip is inserted below the surface of a sample to be tested, with the gun trigger in, and a 0.3 ml sample is extracted. The trigger is released slowly, and any excess on the outside of the tip is wiped off. The contents are injected into the tube 14, the cap 16 immediately replaced, and the tube 14 is shaken vigorously for at least 30 seconds. Then a 5 ml pipette is inserted into the bottle 13, and 5 ml of the color reagent 18 are withdrawn and injected into the tube 14. The tube 14 is again recapped and then is twice inverted and placed in the test tube rack. A timer is immediately set for 30 minutes, and the brown bottle 13 containing the color reagent 18 is returned to the refrigerator.

During the 30-minute period, the colorimeter is turned on and after the colorimeter has warmed up (about 10 minutes), it is calibrated. For this calibration, an empty clean test tube is filled with at least 1 inch of distilled water, and the exterior is wiped clean with a lint-free tissue to remove any moisture or smudges. This tube is inserted in the test tube port of the colorimeter. The wavelength dial of the colorimeter is set to 610 m$\mu$, and the tube is rotated until the white shield is facing the operator. Then the meter zero control knob is turned until the needle reads 0 on the absorbance scale. The instrument is now calibrated.

After the 30-minute wait, the tube 14 is inserted into the colorimeter, with the white shield on the tube facing the operator. The reading is taken and compared with the graph 15 included with the kit 10.

When color chips are used instead of the colorimeter, as in testing for biocidal activity of latex-base paints containing one of the biocides mentioned, the investigator still waits 30 minutes for the color to develop and then compares that color, in good light, directly with the set of color chips.

In the claims the term "oil-water emulsion" includes not only cutting oils and coolants containing oil and water but also the water-based latex emulsion paints.

It will be apparent from the description in this specification that many variations from the exact procedure described are feasible. The description has given the best mode of practicing the invention known to the inventor at this time, but it will be apparent to others skilled in this art that time, temperatures, and amounts can be varied, as well as the procedures involved. Some of the chemicals given have known equivalents for the purposes described; a few examples of these have been given. In any event, the spirit and scope of the invention cover much more than the specific examples given.

I claim:

1. A method for determining the biocide concentration in an oil-water emulsion containing a biocide that in acid aqueous solution liberates material reacting with a modified Schiff's reagent, comprising the following steps:
   1. providing said oil-water emulsion containing a biocide that in acid aqueous solution liberates material reacting with a modified Schiff's reagent,
   2. adding a predetermined sample of said emulsion to a test tube containing (a) a lower aqueous phase solution for breaking said emulsion, and (b) an upper phase of a non-water-miscible solvent for said oil,
   3. shaking the test tube vigorously,
   4. thereafter adding to said test tube and mixing with the liquid therein a predetermined amount of modified Schiff's reagent consisting essentially of an aqueous solution of rosaniline hydrochloride, sodium bisulfite, and hydrochloric acid,
5. permitting the test tube to stand for a predetermined time interval sufficient to separate said phases and to develop color strength in said aqueous phase if said liberated material is present, and
6. reading the color intensity of said aqueous phase, as calibrated for biocide concentration.

2. The method of claim 1 wherein said liberated material is formaldehyde in water 3. The method of claim 1 wherein said aqueous phase solution consists essentially of a strongly acidified solution of magnesium sulfate.

4. The method of claim 3 in which the solution is strongly acidified by acid chosen from the group consisting of sulfuric, nitric, hydrochloric, phosphoric, and acetic acids.

5. The method of claim 1 wherein said non-water-miscible solvent is an alcohol containing from four to 10 carbon atoms.

6. The method of claim 5 wherein said non-water-miscible solvent is chosen from the group consisting of 1-butanol, amyl alcohol, pentanol, and 2-octanol.

7. A method for determining the biocide concentration in an oil-water emulsion containing a biocide that in acidic aqueous solution liberates formaldehyde in water, comprising the following steps:
1. providing an oil-water emulsion containing a biocide that in acidic aqueous solution liberates formaldehyde in water,
2. adding a predetermined small sample of said emulsion to a test tube containing (a) a lower aqueous phase of an aqueous solution of magnesium sulfate and sulfuric acid in predetermined strengths, and (b) an upper phase of 1-butanol,
3. shaking the test tube vigorously,
4. immediately thereafter adding to said test tube and mixing with the liquid therein a predetermined amount of modified Schiff's reagent comprising an aqueous solution of rosaniline hydrochloride, sodium bisulfite, and hydrochloric acid,
5. holding the test tube stationary for a predetermined interval sufficient for development of color, and
5. reading the blue to violet intensity of the aqueous phase, as calibrated for biocide concentration.

8. A method for determining the biocide concentration of an oil-water emulsion containing a biocide that in acidic aqueous solution liberates formaldehyde in water, comprising the following steps:
1. providing an oil-water emulsion containing a biocide that in acidic aqueous solution liberates formaldehyde in water,
2. adding 0.3 ml of said emulsion to a test tube containing (a) a bottom aqueous phase consisting of 2.5 ml of an aqueous solution of magnesium sulfate, at the rate of 50 grams of $MgSO_4 \cdot 7H_2O$ and 25 ml of concentrated $H_2SO_4$ per 100 ml of $H_2O$ and (b) a top phase of 1-butanol,
3. shaking the test tube vigorously for 30 seconds,
4. immediately thereafter adding to said test tube and mixing with the liquid therein 5 ml of modified Schiff's reagent made from 0.2 g of pure rosaniline hydrochloride 2 g of anhydrous sodium bisulfute, and 2 ml of concentrated hydrochloric acid, per 200 ml of water,
5. holding the test tube stationary for 30 minutes, and
6. reading the blue to violet itensity of the aqueous phase, as calibrated for biocide concentration.

9. A method for determining the biocide concentration of an oil-water emulsion containing a biocide reactive in acidic aqueous solution with modified Schiff's reagent, comprising the following steps:
1. providing an oil-water emulsion containing a biocide reactive in acidic aqueous solution with modified Schiff's reagent,
2. breaking the oil emulsion into an oil phase and a water phase, said water phase containing most of said biocide,
3. separating the water and oil phases in space,
4. reacting said water phase with a strong acid,
5. adding a modified Schiff's reagent for formaldehyde detection to said water phase, and
6. reading the intensity of color that develops after a predetermined period of waiting.

10. A method for determining the biocide concentration of an oil-water emulsion containing a biocide that liberates formaldehyde in acid solution, comprising the following steps:
1. providing an oil-water emulsion containing a biocide that liberates formaldehyde in acid solution,
2. breaking the oil emuslion into an oil phase and a water phase, said water phase containing most of said biocide,
3. separating the water and oil phases in space,
4. reacting said water phase with a strong acid,
5. adding a modified Schiff's reagent for formaldehyde detection to said water phase, and
6. reading the intensity of color that develops after a predetermined period of waiting.

11. A method for testing the biocide concentration of a liquid containing a biocide of the type which breaks down in acid aqueous solutions to liberate material reactive with modified Schiff's reagent, comprising:
providing a liquid containing a biocide of the type which breaks down in acid aqueous solutions to liberate material reactive with modified Schiff's reagent,
adding said liquid to a dilute solution of strong aqueous acid,
adding thereto a modified Schiff's reagent made from rosaniline hydrochloride, sodium bisulfite, and hydrochloric acid,
waiting after the addition of the modified Schiff's reagent for a predetermined time period, to enable color to develop, and
reading the color intensity of the solution in terms of biocide concentration.

12. A method for determining the biocide concentration of a liquid containing a biocide that liberates formaldehyde in acid solution, comprising the following steps:
providing a liquid containing a biocide that liberates formaldehyde in acid solution,
adding a sample of said liquid to a solution containing a diluted strong acid and a modified Schiff's reagent for formaldehyde detection, and
reading the intensity of color that develops after a predetermined period of waiting, in terms of biocide concentration.

13. A method for testing the biocide concentration of a liquid containing a biocide selected from the group consisting of 1-(3-chloroallyl)-3,5,7-triaza-1-azoniaadamantane chloride, hexahydro 1,3,5-triethyl-S-triazine, and hexahydro 1,3,5-tris-(2-hydroxyethyl)-S-triazine, comprising:
  providing a liquid containing a biocide selected from the group consisting of 1-(3-chloroallyl)-3,5,7-triaza-1-azoniaadamantane chloride, hexahydro 1,3,5-triethyl-S-triazine, and hexahydro 1,3,4-tris-(2-hydroxyethyl)-S-triazine,
  adding said liquid to a dilute solution of strong aqueous acid,
  adding thereto a modified Schiff's reagent made from rosaniline hydrochloride, sodium bisulfite, and hydrochloric acid,
  waiting after the addition of the modified Schiff's reagent for a predetermined time period, to enable color to develop, and
  reading the color intensity of the solution.

14. A method for determining the biocide concentration of a liquid containing a biocide selected from the group consisting of 1-(3-chlorallyl)-3,5,7-azoniaadamantane chloride, hexahydro 1,3,5-triethyl-S-triazine, and hexahydro 1,3,5-tris-(2-hydroxyethyl)-S-triazine, comprising the following steps:
  providing a liquid containing a biocide selected from the group consisting of 1-(3-chloroallyl)-3,5,7-triaza-1-azoniaadamantane chloride, hexahydro 1,3,5-triethyl-S-triazine, and hexahydro 1,3,5-tris(2-hydroxyethyl)-S-triazine,
  adding a sample of said liquid to a solution containing a diluted strong acid and a modified Schiff's reagent for formaldehyde detection, and
  reading the intensity of color that develops after a predetermined period of waiting.

* * * * *